United States Patent [19]

Cason-Smith

[11] Patent Number: 5,243,075
[45] Date of Patent: Sep. 7, 1993

[54] PROCESS FOR PRODUCING N-CHLOROMETHYL NITRAMINES

[75] Inventor: Donna M. Cason-Smith, Columbia, Md.

[73] Assignee: The United States of America as represented by the Secretary of the Navy, Washington, D.C.

[21] Appl. No.: 912,417

[22] Filed: Jul. 13, 1992

[51] Int. Cl.$^5$ ............................................. C07C 243/02
[52] U.S. Cl. ...................................... 564/109; 564/107
[58] Field of Search ................. 564/107, 109; 562/859

[56] References Cited

U.S. PATENT DOCUMENTS 2,856,429 10/1958 Sauer ..................................... 564/109
4,203,897 5/1980 Kamiya et al. ....................... 540/215
5,079,375 1/1992 Caciagli et al. ...................... 530/337

OTHER PUBLICATIONS

Majer et al. "Syntheses auf Dem Gabiet der Mitamise, etc." *Coll. Czech Chem Comm.* vol. 31, 1966, p. 2547.
Solomons, *Organic Chemistry* 2nd Ed. John Wiley and Sons New York, pp. 768-769.

Primary Examiner—Richard L. Raymond
Assistant Examiner—P. O'Sullivan
Attorney, Agent, or Firm—John D. Lewis; Roger D. Johnson

[57] ABSTRACT

1-acetoxy-2,4,6-trinitro-2,4,6-triazaheptane, 1,7-diacetoxy-2,4,6-trinitro-2,4,6-triazaheptane, or 1,9-diacetoxy-2,4,6,8-tetranitro-2,4,6,8-tetraazanonane is reacted with a mixture of concentrated hydrochloric acid and trifluoroacetic 2,4,6-triazaheptane, 1,7-dichloro-2,4,6-trinitro-2,4,6-triazaheptane, or 1,7-dichloro-2,4,6,8-tetranitro-2,4,6,8-tetraazanonane.

9 Claims, No Drawings

PROCESS FOR PRODUCING N-CHLOROMETHYL NITRAMINES

BACKGROUND OF THE INVENTION

This invention relates to a process for preparing nitramines and more particularly to a process for preparing chloro substituted nitramines.

Monochloromethyl and bis(chloromethyl) substituted nitramines are useful as comonomers in energetic polymers for use in propellant and explosive binders. J. Majer and J. Denkstein, *Collection Czech. Chem. Commun.* 31(b), pp. 2547-57 (1966) disclose a process for making chloromethyl nitramines by bubbling dry hydrochloric acid gas through a solution of N-acetoxymethyl nitramines in anhydrous dioxane at 0° C. The process is expensive and difficult to use. It requires cooling and the use of anhydrous solvents It requires the use of hydrogen chloride gas which is dangerous and requires special handling. Additionally, product separation from the solvent-hydrogen chloride mixture is cumbersome.

Therefore it would be desirable to. provide a safer, less expensive, and easier to use process for producing N-chloromethyl nitramines.

SUMMARY OF THE INVENTION

According, an object of this invention is to provide a new process for making N-chloromethyl nitramines.

Another object of this invention is to provide a safer method of producing N-chloromethyl nitramines without using hydrogen chloride gas.

A further object of this invention is to provide an easier, less expensive method of producing N-chloromethyl nitramines.

These and other objects of this invention are achieved by providing a method of producing N-chloromethyl nitramines by:

reacting an N-acetoxymethyl nitramine which is 1-acetoxy-2,4,6-triazaheptane, 1,7-diacetoxy-2,4,6-trinitro-2,4,6-triazaheptane, or 1,9-diacetoxy-2,4,6,8-tetranitro-2,4,6,8-tetraazanonane with a mixture of concentrated hydrochloric acid and trifluoroacetic acid to produce the corresponding N-chloromethyl nitramine that is 1-chloro-2,4,6-trinitro-2,4,6-triazapheptane, 1,7-dichloro-2,4,6-trinitro-2,4,6-triazapheptane, or 1,9-dichloro-2,4,6,8-tetranitro-2,4,6,8-tetraazanonane, wherein the acid mixture comprises from 10 to 30 weight percent of concentrated hydrochloric acid with trifluoroacetic acid comprising the remainder of the acid mixture. The N-chloromethyl nitramine products are useful as starting materials for the preparation of energetic polymers for explosive and propellant binders.

DETAILED DESCRIPTION OF THE PREFERRED EMBODIMENT

The present invention provides a new process for producing chloromethyl nitramines. In the process a N-acetoxymethyl nitramine is reacted with a mixture of concentrated hydrochloric acid and trifluoroacetic acid to produce the corresponding N-chloromethyl nitramine. The concentrated hydrochloric acid used in this process contains approximately 37 weight percent hydrogen chloride with the remainder being water. For example, (1) 1-acetoxy-2,4,6-trinitro-2,4,6-triazaheptane,

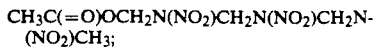

$CH_3C(=O)OCH_2N(NO_2)CH_2N(NO_2)CH_2N(NO_2)CH_3$;

(2) 1,7-diacetoxy-2,4,6-trinitro-2,4,6-triazaheptane, $CH_3C(=O)OCH_2N(NO_2)CH_2N(NO_2)CH_2N(NO_2)CH_2OC(=O)CH_3$; or (3) 1,9-diacetoxy-2,4,6,8-tetranitro-2,4,6,8-tetraazanonane,

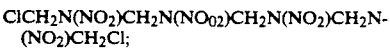

$CH_3C(=O)OCH_2N(NO_2)CH_2N(NO_2)CH_2N(NO_2)CH_2N(NO_2)CH_2OC(=O)CH_3$;

can be reacted with an acid mixture of concentrated hydrochloric acid and trifluoroacetic acid to produce:

(1) 1-chloro-2,4,6-trinitro-2,4,6-triazaheptane, $ClCH_2N(NO_2)CH_2N(NO_2)CH_2N(NO_2)CH_3$;

(2) 1,7-dichloro-2,4,6-trinitro-2,4,6-triazaheptane;

$ClCH_2N(NO_2)CH_2N(NO_2)CH_2N(NO_2)CH_2Cl$; or (3) 1,9-dichloro-2,4,6,8-tetranitro-2,4,6,8-tetraazanonane, $ClCH_2N(NO_2)CH_2N(NO_{02})CH_2N(NO_2)CH_2N(NO_2)CH_2Cl$;

respectively. These preparations are illustrated by examples 1, 2, and 3, respectively.

Examples 4, 5, and 6 disclose methods of preparing the N-acetoxymethyl nitramine starting materials.

The acid mixture is made from concentrated hydrochloric acid and neat (100 percent) trifluoroacetic acid. The acid mixture preferably comprises from about 10 to about 30, more preferably from 15 to 25, and still more preferably about 20 weight percent of concentrated hydrochloric acid with the remainder of the acid mixture being trifluoroacetic acid. Concentrated (37 percent) hydrochloric acid is inexpensive and readily available. It offers a high concentration of HCl with minimal danger of HCl vapors. More dilute forms of hydrochloric acid may be operable in the process, however the efficiency of the process will suffer and the cost of the product N-chloromethyl nitramines will increase accordingly.

This process is preferably run at ambient temperature. At ambient temperature good yields are achieved in reasonable time without the expense of cooling or heating equipment Lower temperatures may be used in the process but this adds cost to the process without any corresponding benefit.

The process is preferably run without the use of solvents or carriers. In examples 1, 2, and 3, the acid mixture is added to the N-acetoxymethyl nitramine staring material However, the procedure may be reversed by adding the N-acetoxymethyl nitramine starting material to the acid mixture.

After the solid product is filtered off, the trifluoroacetic acid (bp 72.4° C.) can be recovered by distillation from the remainder of the reaction mixture (excess HCl, water, and acetic acid). This process may be run as a continuous process.

The general nature of the invention having been set forth, the following examples are presented as specific illustrations thereof. It will be understood that this invention is not limited to these specific examples, but is susceptible to various modifications that will be recognized by one of ordinary skill in the art.

EXAMPLE 1

1-Chloro-2,4,6-trinitro-2,4,6-triazaheptane

To 2.0 g of 1-Acetoxy-2,4,6-trinitro-2,4,6-triazaheptane (6.8 mmol) was added a mixture of 17.8 g trifluoroacetic acid and 4.2 g concentrated hydrochloric acid. After stirring for a few minutes at room temperature the mixture became clear and shortly afterwards a heavy white precipitate formed Stirring was continued overnight at room temperature. The solid was collected by suction filtration, washed with distilled water, and dried in vacuo. Collected was 1.5 g (83%) of 1-chloro-2,4,6-trinitro-2,4,6-triazaheptane.

Mp=139.5–141° C. (from 1,2-dichloroethane/hexanes).

$^1$HMR spectrum (d$_6$-acetonitrile): δ3.57, 5.78, and 5.94. MS (CI): m/e (relative intensity) 292 (M$^+$+NH$_4$, 33%); 290 (M$^+$+NH$_4$, 100%).

Anal. Calcd for C$_4$H$_9$N$_6$O$_6$Cl$_1$: C, 17.62; H, 3.33; N, 30.83; O, 35.21; Cl, 13.01. Found: C, 17.80; H, 3.35; N, 30.98; Cl, 12.85.

EXAMPLE 2

1,7-Dichloro-2,4,6-trinitro-2,4,6-triazaheptane

To 2.0 g of 1,7-Diacetoxy-2,4,6-trinitro-2,4,6-triazaheptane (5.6 mmol) was added a mixture of 17.8 g trifluoroacetic acid and 4.2 g concentrated hydrochloric acid. After stirring for a few minutes at room temperature the mixture became clear and shortly afterwards a heavy white precipitate formed. Stirring was continued overnight at room temperature. The solid was collected by suction filtration, washed with distilled water, and dried in vacuo. Collected was 1.5 g (88%) of 1,7-dichloro-2,4,6-trinitro-2,4,6-triazaheptane.

Mp=144.5–145.5° C. (from 1,2-dichloroethane).

$^1$H NMR spectrum (d6-acetonitrile): δ5.93. MS (CI): m/e (relative intensity) 326 (M$^+$+NH$_4$, 7%); 324 (M$^+$+NH$_4$, 11%); 52 [(CN)$_2$; 100%]. Anal. Calcd. for C$_4$H$_8$N$_6$O$_6$Cl$_2$: C, 15.65; H, 2.63; N, 27.37; O, 31.26; Cl, 23.09. Found: C, 15.57; H, 2.56; N, 27.09; Cl, 23.47.

EXAMPLE 3

1,9-Dichloro-2,4,6,8-tetranitro-2,4,6,8-tetraazanonane

To 2.0 g of 1,9-Diacetoxy-2,4,6,8-tetranitro-2,4,6,8-tetraazanonane (4.7 mmol) was added to a solution of 17.8 g trifluoroacetic acid and 4.2 g concentrated hydrochloric acid. After stirring for a few minutes at room temperature the mixture became clear and shortly afterwards a heavy white precipitate formed. Stirring was continued overnight at room temperature. The solid was collected by suction filtration, washed with distilled water, and dried in vacuo. Collected was 1.7 g (94%) of 1,9-dichloro-2,4,6,8-tetranitro-2,4,6,8-tetraazanonane.

Mp=195–198° C. (from 1,2-dichloroethane). $^1$H NMR spectrum (d$_6$-acetonitrile): δ 5.94 and 5.99.

MS(CI): m/e (relative intensity) 402 (M$^+$+NH$_4$, 1%); 400 (M$^+$+NH$_4$, 8%); 398 (M$^+$+NH$_4$, 12%); 44 (N$_2$O, 100%). Anal. Calcd. for C$_5$H$_{10}$N$_8$O$_8$Cl$_2$: C, 15.76; H, 2.64; N, 29.40; 0, 33.59; Cl, 18.61. Found: C, 15.85; H, 2.62; N, 29.49; Cl, 17.39.

Examples 4, 5, and 6 present prior art methods which were used to prepare the monoacetoxymethyl and diacetoxymethyl nitramine starting materials used in examples 1, 2, and 3. Examples 4, 5 and 6 are quoted from those prior art sources.

Example 4 is quoted from Chemical Abstracts, volume 57, column 13611 (CA 57:13611):

EXAMPLE 4 (prior art)

1-Acetoxy-2,4,6-trinitro-2,4,6-triazaheptane

"Acetate or nitrate of 6-alkyl-2,4,6-trinitro-2,4,6-triazahexanol. Jiri Denkstein and Vladimir Kaderabek. Czech. 98,248, Jan. 15, 1961, Appl. Nov. 13, 1959. The described method is the nitrolysis of N-alkylhexamethylene-tetraminium nitrate, sulfate, or acetate with a mixt. of HNO$_3$ with Ac$_2$O, or anhydride of HNO$_3$. Thus, a mixt. of 30 g N-methylhexamethylenetetraminium nitrate (I) and 49 ml. AcOH added during 15–30 min with stirring at 15°–20° to the mixt. of 52 ml. 98–9% HNO$_3$, and 48 ml. Ac$_2$O under stirring, the temp. increased to 75° and kept 15 min. gave after cooling to 20°–5° 22.2 g cryst. 6-methyl-2,4,6-trinitro-2,4,6-triazahexanol (II). The reactin mixt. dild. with water gave addnl. 5.3 g II. The total yield was 27.5 g of a product, m. 151°–3°, i.e., 68% of theory calcd. on I."

Examples 5 and 6 are quoted from page 2772 of an article by W.E. Bachmann, W.J. Horton, E.L. Jenner, N.W. MacNaughton and L.B. Scott, titled, "Cyclic and Linear Nitramines Formed by Nitrolysis of Hexamine," which appeared in the Journal of the American Chemical Society, Volume 73, No. 6 (June 1951), pages 2769–2773, herein incorporated in its entirety.

EXAMPLE 5 (prior art)

1,7-Diacetoxy-2,4,6-trinitro-2,4,6-triazaheptane

"1,7-Diacetoxy-2,4,6-trinitro-2,4,6-triazaheptane (IV).—A series of runs were made in which hexamine, nitric acid and acetic anhydride were brought together under various conditions. In (a) is given a procedure in which ease of obtaining a pure compound rather than yield is emphasized. In (b) is given a procedure which employs hexamine dinitrate.

"(a) Forty-five cc. of 98% nitric acid was added gradually with stirring to 120 cc. of acetic anhydride (in a three-necked flask equipped with a thermometer and a paddle stirrer) which was kept at 15°–20° by means of an ice-bath. A solution of 33.6 g of hexamine in 55 cc. of glacial acetic acid was added continuously to the stirred mixture at 15°–20° in twenty minutes. The resulting mixture was heated in the course of fifteen minutes to 75°; the clear solution was stirred as it cooled to room temperature; at about 70° a few crystals of IV were introduced. After standing at room temperature for twelve hours, the well-formed crystals of IV were collected on a filter and washed with acetic acid. The moist product was dissolved in 100 cc. of hot acetic acid, and the solution after seeding was allowed to cool; yield of colorless plates 43 g. (51%); m.p. 153–154.5°.

"The original mother liquor contained additional IV and much water-insoluble gum. The whole was disposed of by converting it into water-soluble products by addition of 700 cc. of water followed by simmering on a steam-bath for three to five hours.

"By omitting the heating to 70°, a 48-g. first crop was obtained which gave 34 g of IV with m.p. 154–155 on recrystallization."

(The reference also discloses a method of making this compound from hexamine dinitrate.)

EXAMPLE 6 (prior art)

1,9-Diacetoxy-2,4,6,8-tetranitro-2,4,6,8-tetraazanonane

"1,9-Diacetoxy-2,4,6,8-tetranitro-2,4,6,8-tetrazanonane (V). Twenty cc. of acetic acid was placed in a four-necked 1-1 flask equipped with a thermometer, paddle stirrer and two burets, and the flask was immersed in an ice-bath. A solution of 33.6 g of hexamine in 55 cc of acetic acid and a cold freshly-prepared mixture (see above) of 21 cc of 98% nitric acid and 60 cc of acetic anhydride were added continuously and equivalently in six minutes to the stirred acetic acid; the temperature of the reaction mixture was kept at 30°. After being stirred at 30° for one-half hour more, the thick mixture was poured into a dry beaker (hood). Acetic anhydride (150 cc) was added to the uncleaned reaction flask; 40 cc of 98% nitric acid was added with cooling, and the four-state reaction product (contained in the beaker) was added in three to five minutes; the temperature was kept at 25°-30°. Acetic anhydride (50 cc) was used to transfer the residual material in the beaker into the reaction mixture.

"The stirred reaction mixture was heated slowly to 70°; brown fumes were evolved and some solid remained undissolved. The bath was removed and the mixture was stirred as it cooled to room temperature. After two hours the product was collected on a filter and washed with acetic acid; yield 41.2 g; m.p. 174°-177°. Recrystallization from 600 cc of acetic acid yielded colorless nacreous plates of V; yield 33.1 g. (32%); m.p. 182.5°-183.5°."

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A process for producing N-chloromethyl nitramines comprising
   (1) contacting an N-acetoxymethyl nitramine that is 1-acetoxy-2,4,6-trinitro-2,4,6-triazaheptane, 1,7-diacetoxy-2,4,6-trinitro-2,4,6-triazaheptane, or 1,9-diacetoxy-2,4,6,8-tetranitro-2,4,6,8-tetraazanonane with a mixture of concentrated hydrochloric acid and trifluoroacetic acid to produce the corresponding N-chloromethyl nitramine that is 1-chloro-2,4,6-trinitro-2,4,6-triazaheptane, 1,7-dichloro-2,4,6-trinitro-2,4,6-triazaheptane, or 1,9-tetranitro-2,4,6,8-tetraazanonane,
   wherein the acid mixture comprises from 10 to 30 weight percent of concentrate hydrochloric acid with trifluroacetic acid comprising the remainder; and
   (2) isolating the N-chloromethyl nitramine product.

2. The process of claim 1 wherein the N-acetoxymethyl nitramine starting material is 1-acetoxy-2,4,6-trinitro-2,4,6-triazaheptane.

3. The process of claim 1 wherein the N-acetoxymethyl nitramine starting material is 1,7-diacetoxy-2,4,6-trinitro-2,4,6-triazaheptane.

4. The process of claim 1 wherein the N-acetoxymethyl nitrate starting material is 1,9-diacetoxy-2,4,6,8-tetranitro-2,4,6,8-tetrazanonane.

5. The process of claim 1 wherein the acid mixture comprises from 15 to 25 weight percent of concentrated hydrochloric acid with trifluoro acetic acid comprising the remainder of the mixture.

6. The process of claim 5 wherein the acid mixture comprises about 20 weight percent concentrated hydrochloric acid with trifluoracetic acid comprising the remainder of the acid mixture.

7. The process of claim 1 which is run at ambient temperature.

8. The process of claim 1 wherein after step (2) the trifluoroacetic acid is recovered.

9. The process of claim 9 wherein the trifluoroacetic acid is recovered by distillation.

* * * * *